United States Patent
Shepherd et al.

(10) Patent No.: US 12,125,278 B2
(45) Date of Patent: Oct. 22, 2024

(54) INFORMATION EXTRACTION FROM LIVE ONLINE SESSIONS

(71) Applicant: Dell Products L.P., Round Rock, TX (US)

(72) Inventors: Michael Shepherd, Leander, TX (US); Jonathan Whitson, Oklahoma City, OK (US)

(73) Assignee: DELL PRODUCTS L.P., Round Rock, TX (US)

( * ) Notice: Subject to any disclaimer, the term of this patent is extended or adjusted under 35 U.S.C. 154(b) by 424 days.

(21) Appl. No.: 17/678,758

(22) Filed: Feb. 23, 2022

(65) Prior Publication Data
US 2023/0267734 A1 Aug. 24, 2023

(51) Int. Cl.
*G06V 20/40* (2022.01)
*G06V 10/764* (2022.01)
(Continued)

(52) U.S. Cl.
CPC ............ *G06V 20/41* (2022.01); *G06V 10/764* (2022.01); *G06V 10/82* (2022.01); *G16H 40/67* (2018.01)

(58) Field of Classification Search
CPC ...... G06V 20/41; G06V 10/764; G06V 10/82; G06V 10/25; G06V 10/62; G06V 40/168; G06V 40/172; G06V 40/176; G06V 10/454; G06V 10/54; G06V 10/774; G06V 30/18057; G16H 40/67; G16H 10/60; G16H 15/00; G16H 30/40; G16H 50/20; G16H 50/70; G16H 50/80; A61B 5/0008;
(Continued)

(56) References Cited

U.S. PATENT DOCUMENTS 9,532,004 B1 * 12/2016 Metter ................... H04N 7/152
11,195,619 B2 * 12/2021 Baughman ............. G06N 20/00
(Continued)

FOREIGN PATENT DOCUMENTS

CN 112085630 A 12/2020

OTHER PUBLICATIONS

Notice of Allowance mailed Jul. 27, 2023 for U.S. Appl. No. 17/581,594, 20 pages.
(Continued)

*Primary Examiner* — Jose L Couso
(74) *Attorney, Agent, or Firm* — Amin, Turocy & Watson, LLP (57) ABSTRACT

A system can identify time-series bio telemetry data that corresponds to a first user of an online session, wherein the time-series bio telemetry data identifies a first user engagement of the first user. The system can identify a first video recording of the online session, wherein the first video recording is representative of a first video of the first user. The system can input the time-series bio telemetry data and the first video recording as a first input to a neural network model to produce a trained neural network model, wherein the trained neural network model is configured to classify a second user engagement from a second video recording representative of a second video of a second user. The system can classify the second user engagement of the second user comprising inputting the second video recording as a second input to the trained neural network model.

20 Claims, 9 Drawing Sheets

(51) Int. Cl.
*G06V 10/82* (2022.01)
*G16H 40/67* (2018.01)

(58) Field of Classification Search
CPC ... A61B 5/0013; A61B 5/0075; A61B 5/0077; A61B 5/01; A61B 5/015; A61B 5/7264; A61B 5/7282; A61B 5/743; G06N 3/02; G06N 3/08–088; G06N 3/0445; G06N 3/0454; G06N 3/4046; G06N 7/00; G06N 7/01; G06N 20/00; G06T 3/4046; G06T 5/60; G06T 9/002; G06T 2207/20076; G06T 2207/20081; G06T 2207/20084; G06K 7/1482; Y10S 128/925

See application file for complete search history.

(56) References Cited

U.S. PATENT DOCUMENTS

| | | | |
|---|---|---|---|
| 11,720,814 B2* | 8/2023 | Shen | G06N 20/00 706/12 |
| 11,782,739 B2* | 10/2023 | Singh | G06F 9/451 715/704 |
| 2013/0258042 A1 | 10/2013 | Shun et al. | |
| 2017/0177928 A1 | 6/2017 | Cunico et al. | |
| 2019/0109660 A1 | 4/2019 | Akins, III | |
| 2020/0076566 A1 | 3/2020 | Andrade Alfonseca et al. | |
| 2021/0038088 A1* | 2/2021 | Atallah | A61B 5/14551 |
| 2021/0098110 A1* | 4/2021 | Periyasamy | G16H 20/70 |
| 2021/0271864 A1* | 9/2021 | Litvin | G06V 10/764 |
| 2022/0079439 A1* | 3/2022 | Heislop | A61B 5/0008 |
| 2022/0086393 A1* | 3/2022 | Peters | G06V 20/41 |
| 2023/0147584 A1* | 5/2023 | Asgekar | H04L 65/1083 382/103 |
| 2023/0215171 A1* | 7/2023 | Kim | G06V 20/41 382/107 |
| 2023/0219007 A1* | 7/2023 | Rudi | A63F 13/67 463/42 |
| 2023/0225612 A1* | 7/2023 | McGrath | A61B 3/00 351/208 |

OTHER PUBLICATIONS

Shepherd, et al. "Bio-Telemetry Extraction from Online Sessions" U.S. Appl. No. 17/581,594, filed Jan. 21, 2022, 39 pages.
Shepherd, et al. "Determining Loss of Focus in Online Sessions" U.S. Appl. No. 17/581,263, filed Jan. 21, 2022, 39 pages.
Office Action mailed Mar. 17, 2023 for U.S. Appl. No. 17/581,594, 11 pages.
Notice of Allowance mailed Feb. 17, 2023 for U.S. Appl. No. 17/581,263, 21 pages.

* cited by examiner

INFORMATION EXTRACTION FROM LIVE
ONLINE SESSIONS COMPONENT 412

402

| WAVE | STATE OF CONSCIOUSNESS | FREQUENCY (HZ) | PSYCHOLOGICAL STATE |
|---|---|---|---|
| LOW ALPHA | CONSCIOUSNESS AND SUBCONSCIOUS LEVEL | 8-9 | RELAXED |
| HIGH ALHA | CONSCIOUSNESS AND SUBCONSCIOUS LEVEL | 10-12 | RELAXED |
| LOW BETA | LEVEL OF CONSCIOUSNESS | 13-17 | CONCENTRATION |
| HIGH BETA | LEVEL OF CONSCIOUSNESS | 18-30 | CONCENTRATION |

IN RESPONSE TO DETERMINING TO CAPTURE BIO TELEMETRY DATA ASSOCIATED WITH A FIRST CLIENT COMPUTING DEVICE, SYNCHRONIZING A SECOND CLOCK TIME OF THE CLIENT COMPUTING DEVICE WITH A FIRST CLOCK TIME MAINTAINED BY A NETWORK TIME PROTOCOL SERVER, WHEREIN THE CLIENT COMPUTING DEVICE IS CONFIGURED TO CAPTURE BIO TELEMETRY DATA OF A FIRST USER ASSOCIATED WITH THE FIRST CLIENT COMPUTING DEVICE, AND WHEREIN THE FIRST USER IS ASSOCIATED WITH A FIRST USER ACCOUNT 804

IN RESPONSE TO DETERMINING TO CAPTURE BIO TELEMETRY DATA ASSOCIATED WITH A SECOND CLIENT COMPUTING DEVICE, SYNCHRONIZING A THIRD CLOCK TIME OF THE CLIENT COMPUTING DEVICE WITH THE FIRST CLOCK TIME, WHEREIN THE SECOND CLIENT COMPUTING DEVICE IS CONFIGURED TO CAPTURE BIO TELEMETRY DATA OF A SECOND USER ASSOCIATED WITH THE SECOND CLIENT COMPUTING DEVICE 806

SYNCHRONIZING THE BIO TELEMETRY DATA OF THE FIRST USER WITH THE BIO TELEMETRY DATA OF THE SECOND USER BASED ON THE SECOND CLOCK TIME AND THE THIRD CLOCK TIME 808

INFORMATION EXTRACTION FROM LIVE ONLINE SESSIONS

BACKGROUND

Online sessions can comprise multi-participant video meetings conducted with computers that communicate across a communications network.

SUMMARY

The following presents a simplified summary of the disclosed subject matter in order to provide a basic understanding of some of the various embodiments. This summary is not an extensive overview of the various embodiments. It is intended neither to identify key or critical elements of the various embodiments nor to delineate the scope of the various embodiments. Its sole purpose is to present some concepts of the disclosure in a streamlined form as a prelude to the more detailed description that is presented later.

An example system can operate as follows. The system can identify time-series bio telemetry data that corresponds to a first user of an online session, wherein the time-series bio telemetry data identifies a first user engagement of the first user. The system can identify a first video recording of the online session, wherein the first video recording is representative of a first video of the first user. The system can input the time-series bio telemetry data and the first video recording as a first input to a neural network model to produce a trained neural network model, wherein the trained neural network model is configured to classify a second user engagement from a second video recording representative of a second video of a second user. The system can classify the second user engagement of the second user comprising inputting the second video recording as a second input to the trained neural network model.

A method can comprise identifying, by a system comprising a processor, time-series bio telemetry data that corresponds to a first user of an online session. The method can further comprise identifying, by the system, a first video recording of the first user of the online session. The method can further comprise providing, by the system, the time-series bio telemetry data and the first video recording as a first input to a neural network model to produce a trained neural network model, wherein the trained neural network model is configured to classify user engagement from a second video recording of a second user. The method can further comprise classifying, by the system, the user engagement of the second user based on an output from providing the second video as a second input to the trained neural network model.

An example non-transitory computer-readable medium can comprise instructions that, in response to execution, cause a system comprising a processor to perform operations. These operations can comprise identifying time-series bio telemetry data associated with a first user of an online session. These operations can further comprise accessing a first video recording comprising a first video of the online session. These operations can further comprise based on the time-series bio telemetry data and the first video recording, training a neural network model to produce a trained neural network model that is configured to classify user engagement of different users. These operations can further comprise classifying a user engagement of a second user based on a result of inputting a second video of the second user to the trained neural network model.

BRIEF DESCRIPTION OF THE DRAWINGS

Numerous embodiments, objects, and advantages of the present embodiments will be apparent upon consideration of the following detailed description, taken in conjunction with the accompanying drawings, in which like reference characters refer to like parts throughout, and in which.

DETAILED DESCRIPTION

Overview

A convolutional neural network (CNN) long short-term memory network (LTSM) neural network can be leveraged to capture visual information from learners in an online session. This information can be used in tandem with bio telemetry data to predict learner engagement based on facial patterns.

Within a domain of education, it can be standard practice to report on a student's completion of a piece of course material. A next level of analytics can show what actions the student took in the course. For example, it can be determined whether the student skipped through e-learning material, whether the student missed certain questions from assessments, etc. This level of behavior-level analytics within a learning event can be valuable data. A problem with this approach to analyzing learner engagement can be that it can be heavily reliant on assumptions.

The present techniques can be implemented to provide for improved learner analysis by capturing facial information from virtual instructor led courses. This facial information can be correlated with bio telemetry data to more accurately determine learner engagement.

The present techniques can be implemented to track learner engagement globally, across many delivered courses, with an ability to identify areas of courses with empirically a least level of engagement.

A problem with prior approaches can be that there is not a way to automate quality assurance (QA) of a virtual course.

Another problem with prior approaches can be that prior approaches are strictly set to an e-learning modality, and they do not include virtual instructor or classroom led training.

The present techniques can be implemented to deploy a virtual agent to capture facial information from a virtual class for a purpose of identifying learner engagement. The present techniques can be implemented to process a video of a virtual class through a CNN LSTM network to encode a learner's facial patterns across times within an education domain.

Example Architectures

Figure 1:
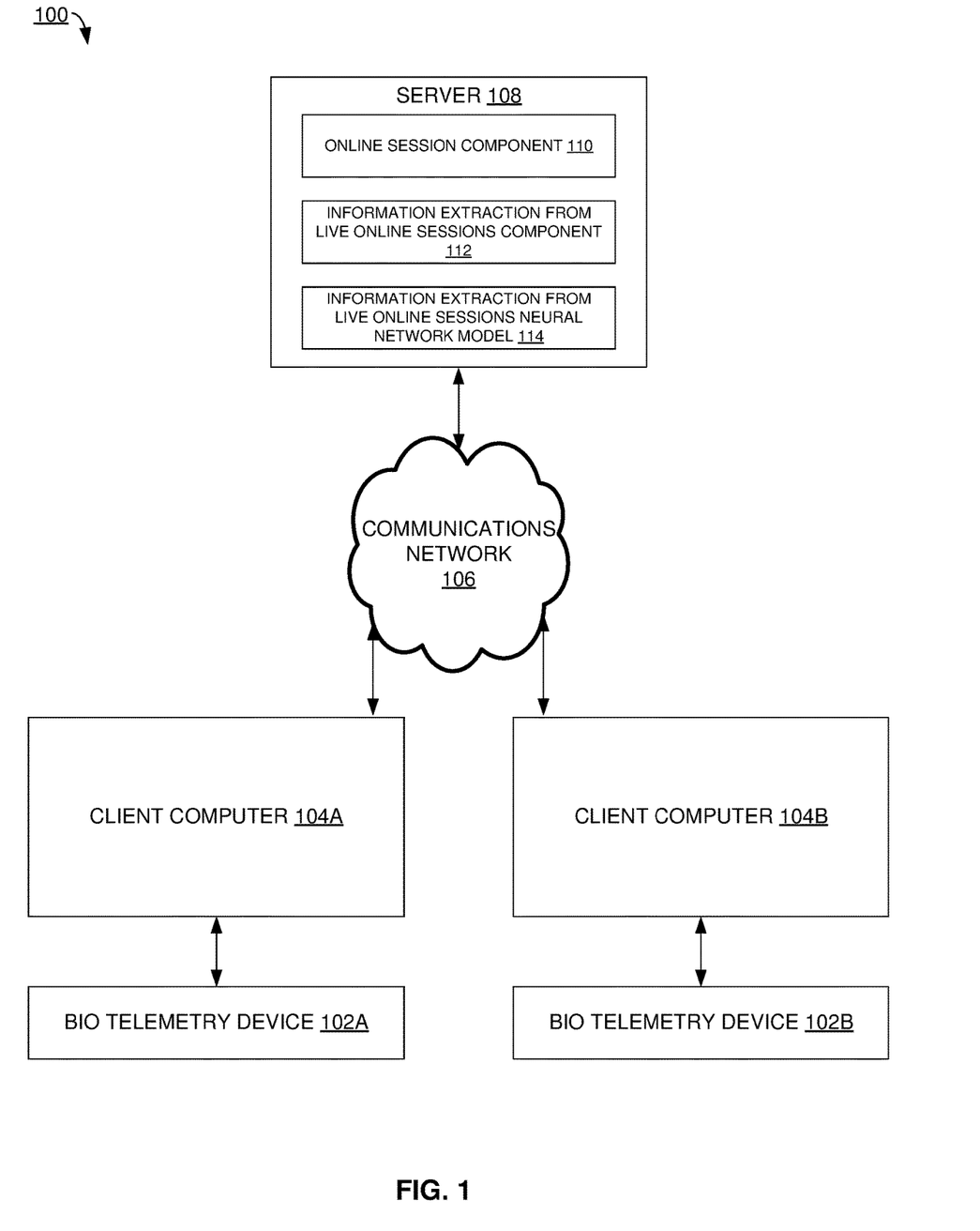
FIG. 1 illustrates an example system architecture that can facilitate information extraction from live online sessions, in accordance with an embodiment of this disclosure.

FIG. 1 illustrates an example system architecture 100 that can facilitate information extraction from live online sessions, in accordance with an embodiment of this disclosure.

System architecture comprises bio telemetry device 102A, bio telemetry device 102B, client computer 104A, client computer 104B, communications network 106, and server 108. Server 108 comprises online session component 110, information extraction from live online sessions component 112, and information extraction from live online sessions neural network model 114.

Figure 9:
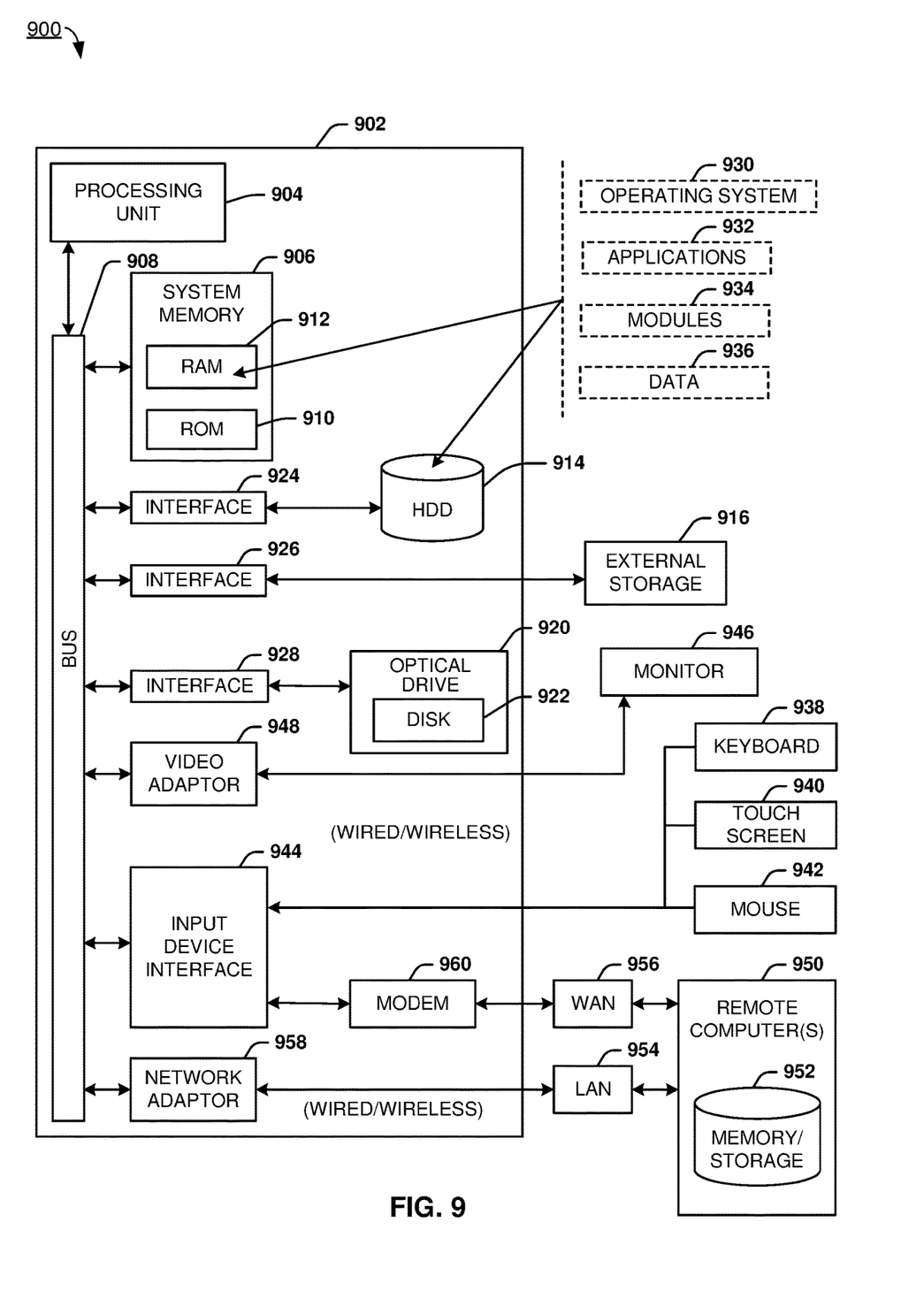
FIG. 9 illustrates an example block diagram of a computer operable to execute an embodiment of this disclosure.

Each of bio telemetry device 102A, bio telemetry device 102B, client computer 104A, client computer 104B, and server 108 can be implemented with part(s) of computing environment 900 of FIG. 9. Communications network 106 can comprise a computer communications network, such as the Internet.

Figure 6:
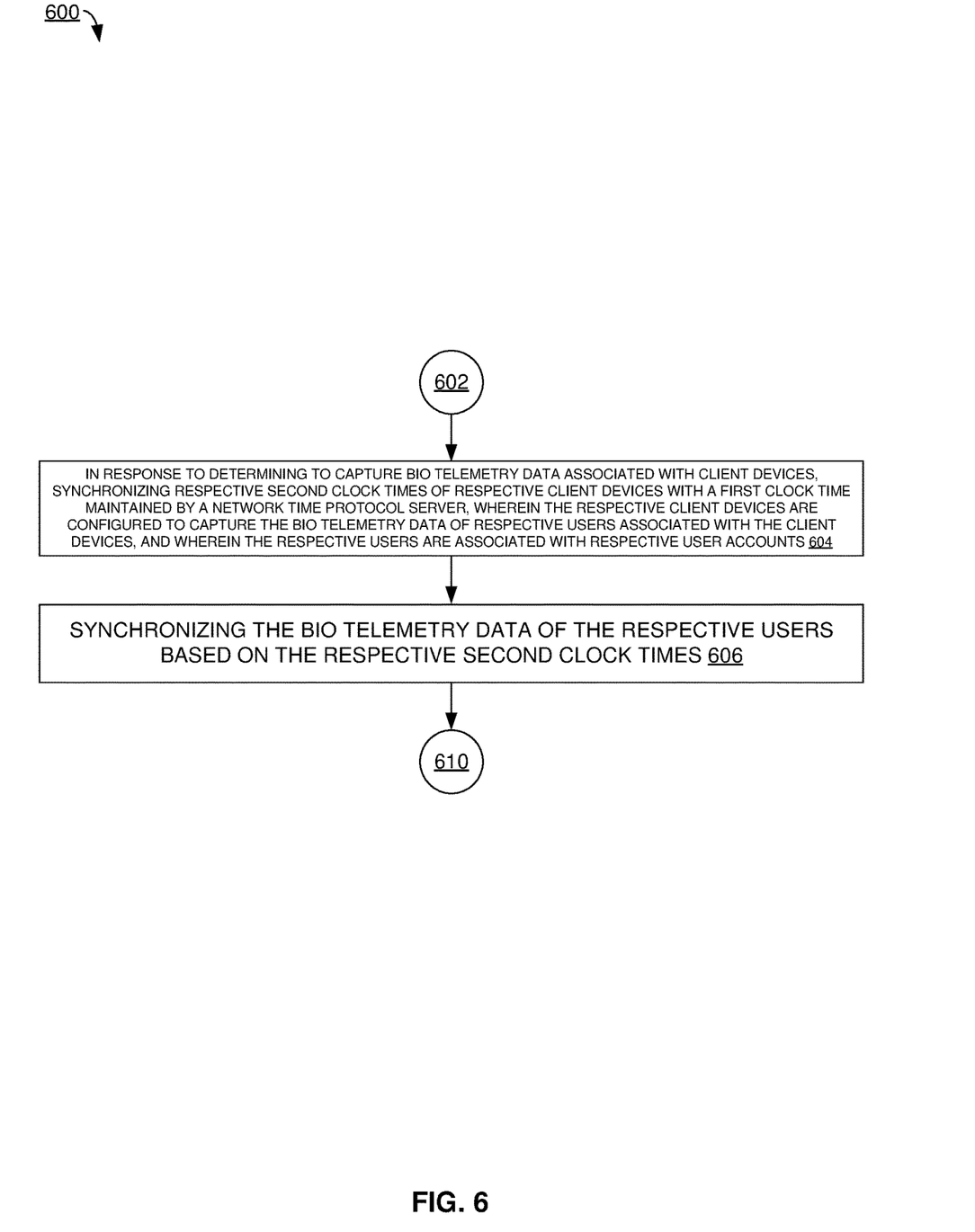
FIG. 6 illustrates an example process flow that can facilitate information extraction from live online sessions, in accordance with an embodiment of this disclosure.
Figure 7:
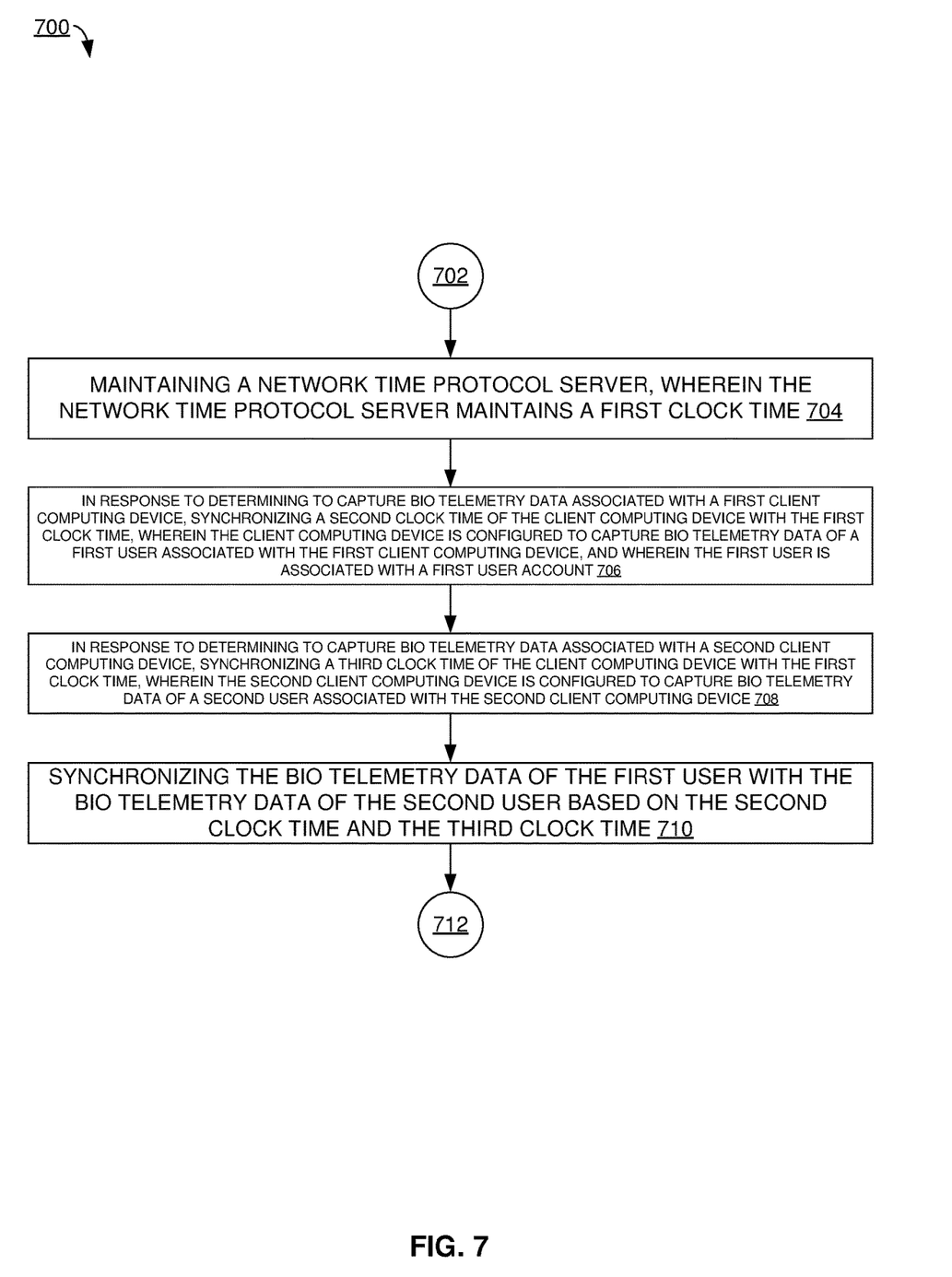
FIG. 7 illustrates an example process flow that can facilitate information extraction from live online sessions, in accordance with an embodiment of this disclosure.
Figure 8:
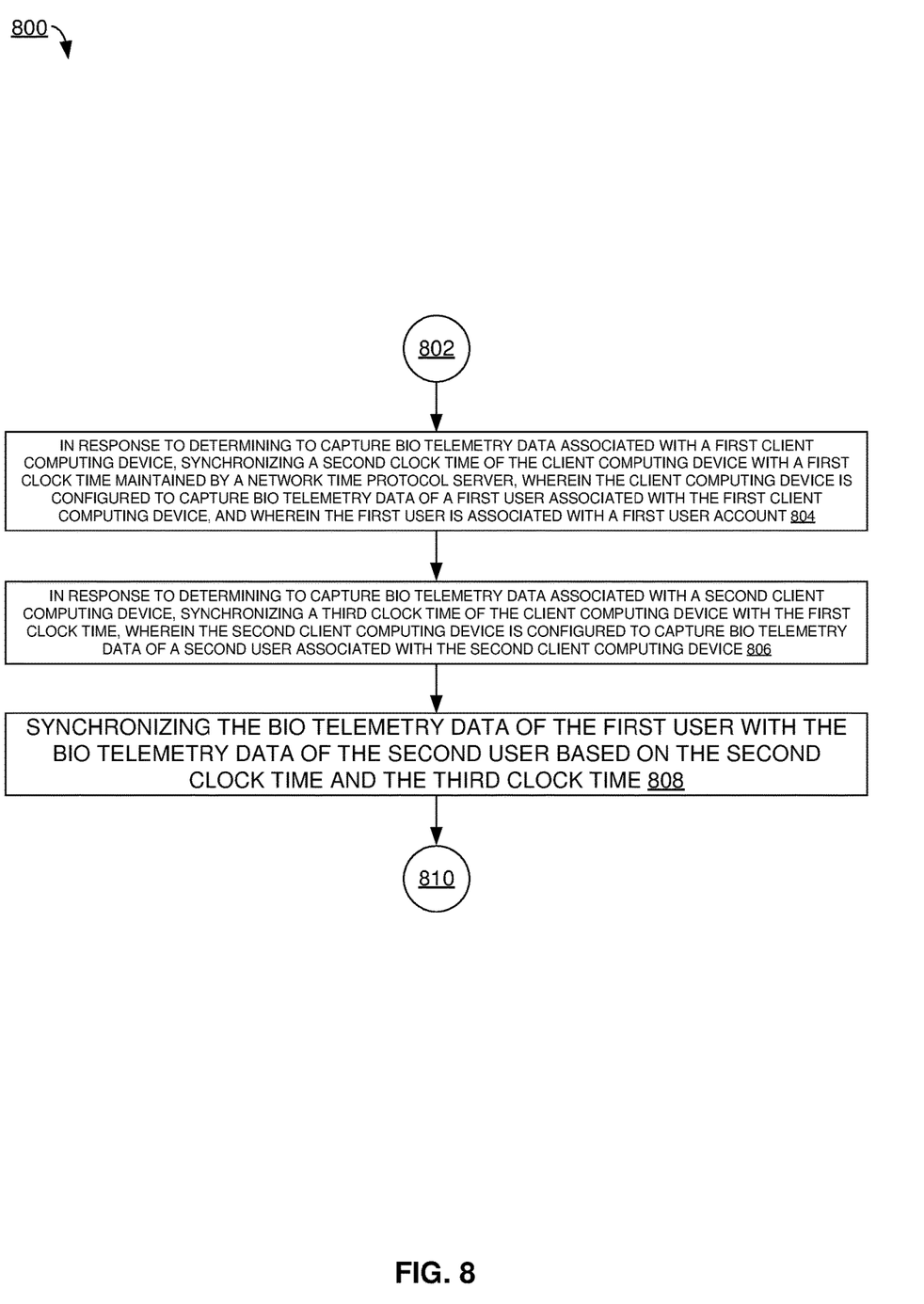
FIG. 8 illustrates an example process flow that can facilitate information extraction from live online sessions, in accordance with an embodiment of this disclosure.

In some examples, information extraction from live online sessions component 112 can implement part(s) of the process flows of FIGS. 6-8 to facilitate information extraction from live online sessions.

Each of bio telemetry device 102A and bio telemetry device 102B can capture bio telemetry data (e.g., EEG data) from users as users participate in an online session that is served by online session component 110, via their respective computers, client computer 104A and client computer 104B. Bio telemetry device 102A and bio telemetry device 102B can communicate with client computer 104A and client computer 104B, respectively, to share this bio telemetry data via a near field communication protocol, such as a Bluetooth communications protocol.

It can be that online session component 110 conducts an online session with user accounts associated with client computer 104A and client computer 104B respectively. Respective users of client computer 104A and client computer 104B can opt in to sharing bio telemetry data about their engagement (e.g., electroencephalography). This bio telemetry data can be gathered, respectively, by bio telemetry device 102A, at bio telemetry device 102B. Bio telemetry device 102A, at bio telemetry device 102B can be communicatively coupled with client computer 104A and client computer 104B, respectively.

A recording of the online session (which can include a video of one or more users providing bio telemetry data) can be generated by online session component 110. information extraction from live online sessions component 112 can use the recording as well as the bio telemetry data as input to train live online sessions neural network model 114. The bio telemetry data can be used to indicate user engagement, and corresponding facial expressions or actions by a user in the recording can be identified by the model as correspondingly indicating user engagement.

Once trained, live online sessions neural network model 114 can take another recording of an online session as input and identify user engagement (e.g., spots of high or low engagement) as output.

It can be appreciated that system architecture 100 is one example system architecture for extracting information from live online sessions, and that there can be other system architectures that facilitate determining loss of focus in online sessions. For example, online session component 110 and information extraction from live online sessions component 112 can be implemented on different computers.

Figure 2:
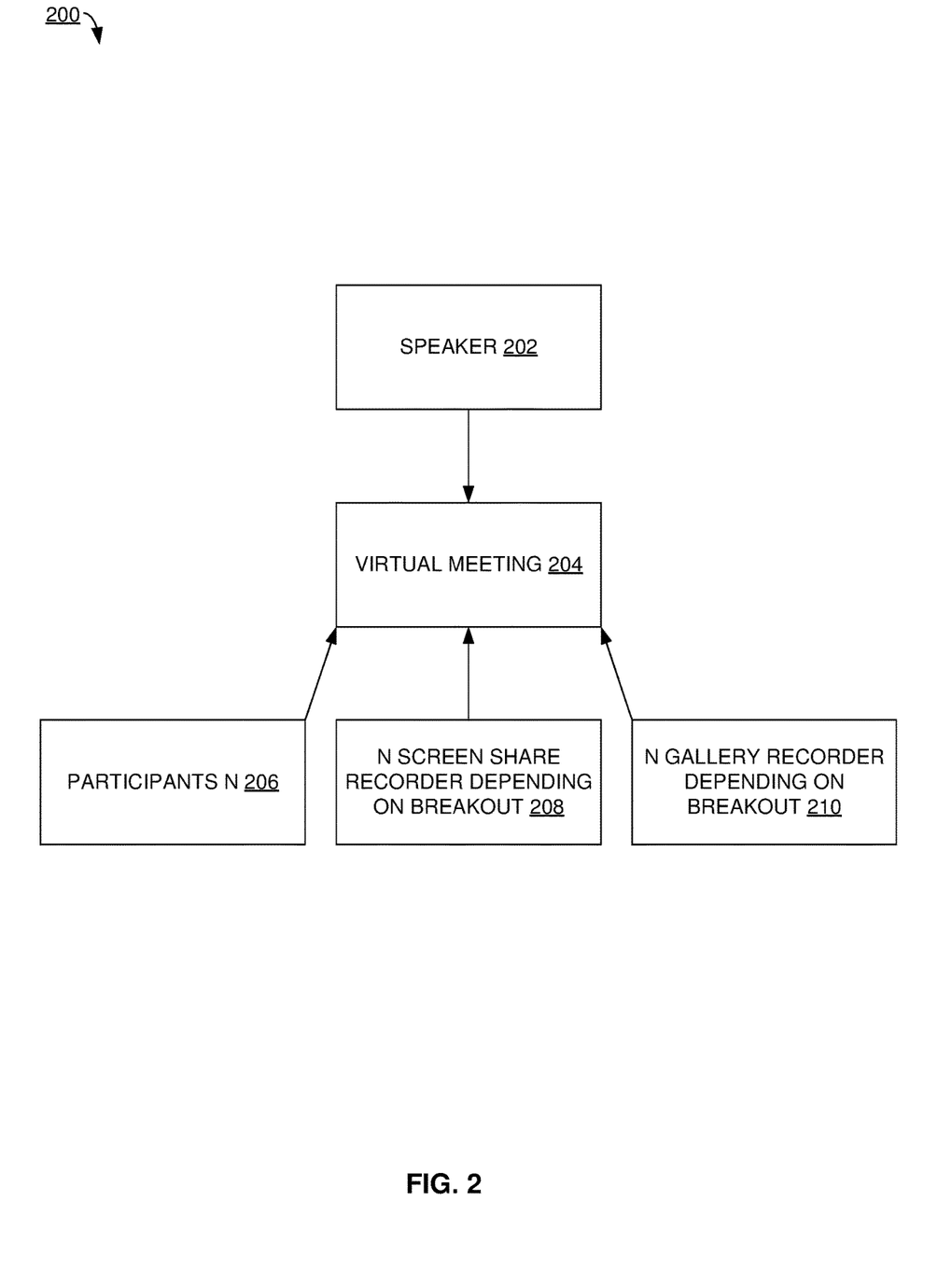
FIG. 2 illustrates an example system architecture for a virtual agent attending an online session, and that can facilitate information extraction from live online sessions, in accordance with an embodiment of this disclosure.

FIG. 2 illustrates an example system architecture 200 for a virtual agent attending an online session, and that can facilitate information extraction from live online sessions, in accordance with an embodiment of this disclosure. In some examples, parts of system architecture 200 can be implemented by server 108 of FIG. 1.

System architecture 200 comprises speaker 202, virtual meeting 204, participants N 206, N screen share recorder depending on breakout 208, N gallery recorder depending on breakout 210, and information extraction from live online sessions component 212. Virtual meeting 204 can comprise a virtual meeting hosted by online session component 110 of FIG. 1.

Speaker 202 can comprise an identification of a current speaker in virtual meeting 204. Participants N 206 can comprise an identification of participants to virtual meeting 204 (and there can be N number of such participants). N screen share recorder depending on breakout 208 can comprise a component that records up to N screen shares of virtual meeting 204 (e.g., a share by a participant of the contents of his or her device; where breakout sessions in virtual meeting 204 can affect a number of concurrent screen shares). N gallery recorder depending on breakout 210 can comprise a component that records up to N galleries of virtual meeting 204 (e.g., a video of a participant of participants N 206; where a number of gallery views can vary, for example, based on whether a user has his or her video camera enabled). Information extraction from live online sessions component 212 can be similar to information extraction from live online sessions component 112 of FIG. 1.

Within a realm of education, there can be an ability to deliver course content via a virtual modality. The present techniques can be agnostic to which of multiple online session platforms is used, where a virtual agent is implemented that records a learner's webcam video. These recordings can be used to classify learner engagement.

Figure 3:
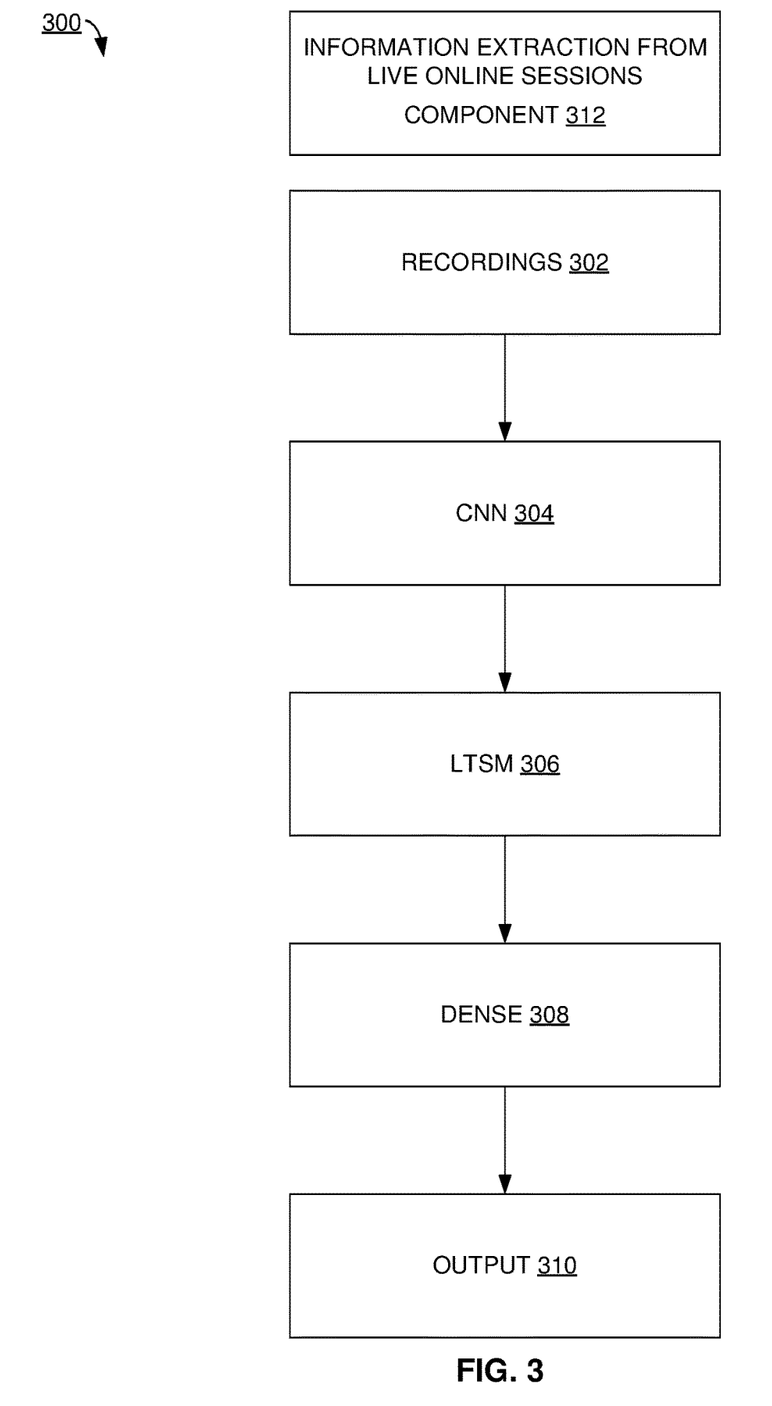
FIG. 3 illustrates an example system architecture for training a model, and that can facilitate information extraction from live online sessions, in accordance with an embodiment of this disclosure.

FIG. 3 illustrates an example system architecture 300 for training a model, and that can facilitate information extraction from live online sessions, in accordance with an embodiment of this disclosure. In some examples, parts of system architecture 300 can be implemented to train information extraction from live online sessions neural network model 114 of FIG. 1.

System architecture 300 comprises recordings and bio telemetry data 302, convolutional neural network 304, long short-term memory network 306, dense 308, output 310, and information extraction from live online sessions component 312.

Recordings and bio telemetry data 302 can comprise recordings of an online session (such as virtual meeting 204 of FIG. 2), and bio telemetry data gathered from bio telemetry device 102A and bio telemetry device 102B of FIG. 1.

In some examples, the recordings can be provided as an X variable and bio telemetry data can be provided as a Y variable in a cartesian coordinate system.

CNN 304 can comprise a convolutional neural network that receives recordings and bio telemetry data 302. An output of CNN 304 can be provided to LTSM 306, which can generally comprise another type of neural network. An output of LTSM 306 can be provided to dense 308, which can generally comprise a dense layer of a neural network. An output of dense 308 can be output 310, which can comprise an output of a neural network. Information extraction from live online sessions component 312 can be similar to information extraction from live online sessions component 112 of FIG. 1.

Recordings and bio telemetry data 302 can be used to train a neural network. For example, the bio telemetry data of recordings and bio telemetry data 302 can indicate a user's level of engagement, and the neural network can be trained to associate an image of the user in recordings and bio telemetry data 302 with a particular level of engagement.

Training a model to classify learner engagement can be implemented as follows. Training data can be generated via a series of classes. Learners in these classes can wear bio telemetry devices. Learners can go about a course as they generally would, with various levels of engagement over time being stored as a Y variable, while a X variable is a series of frames from a recording of the learner and the session share. Transcripts can be tagged with a speaker and a text transcription of their audio, as well as text of screen imagery.

Figure 4:
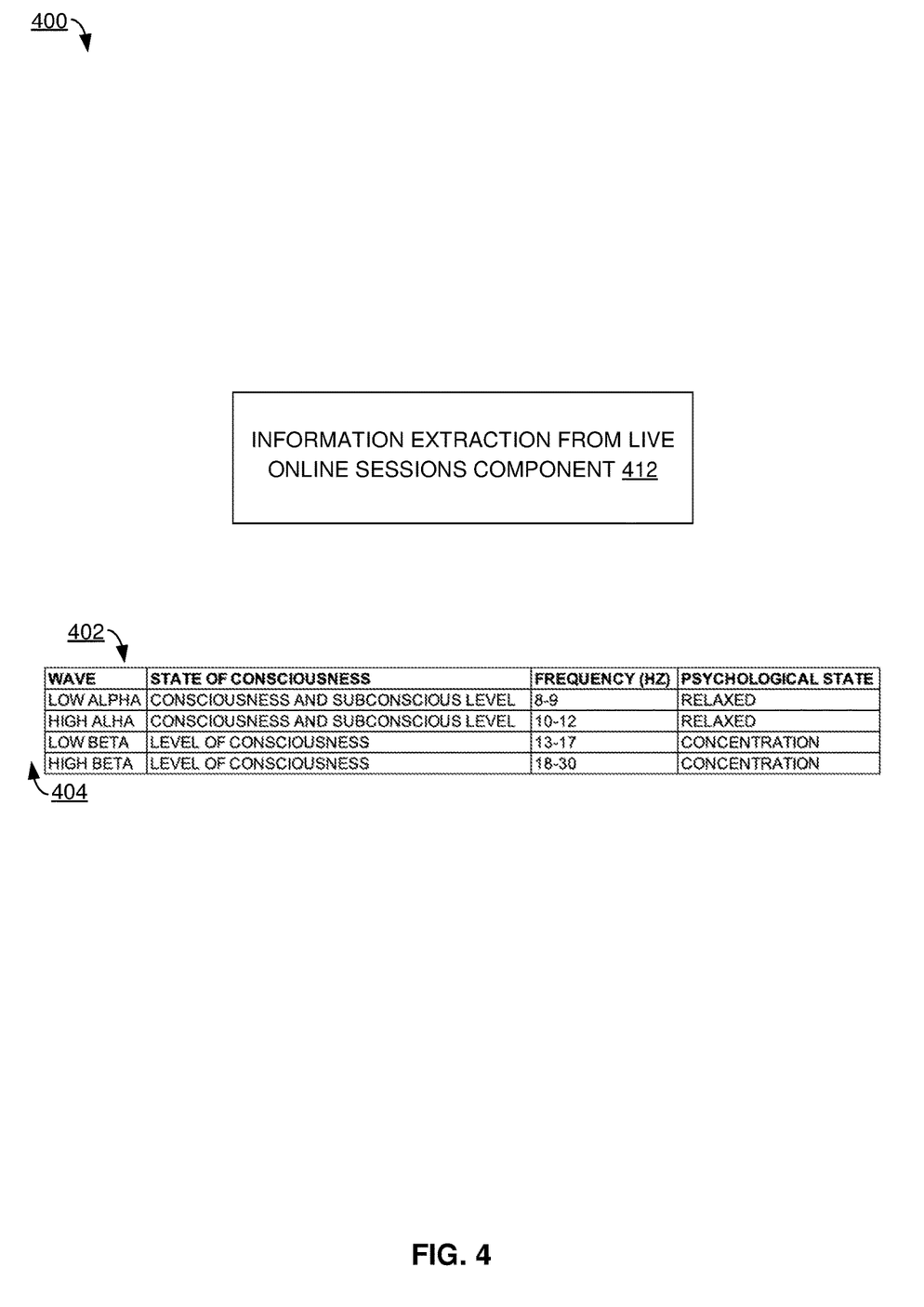
FIG. 4 illustrates an example system architecture for classifying electroencephalography data, and that can facilitate information extraction from live online sessions, in accordance with an embodiment of this disclosure.

FIG. 4 illustrates an example system architecture 400 for classifying electroencephalography data, and that can facilitate information extraction from live online sessions, in accordance with an embodiment of this disclosure. In some examples, parts of system architecture 400 can be implemented to train information extraction from live online sessions neural network model 114 of FIG. 1.

System architecture 400 comprises columns 402 and rows 404 of a table, and information extraction from live online sessions component 312. The table can identify what particular bio telemetry data indicates as far as user engagement.

In EEG data, beta brain waves can be associated with heightened concentration, whereas alpha brain waves can indicate learning. The present techniques can be implemented to monitor movement of these waves in participants, and from that monitored movement, create a personalized attention indicator that assesses a baseline of non-attentiveness and monitors for heights of attentiveness. This data can be normalized to a range of [0, 1], where 0 can represent no attentiveness, and 1 can represent a height of attentiveness.

Figure 5:
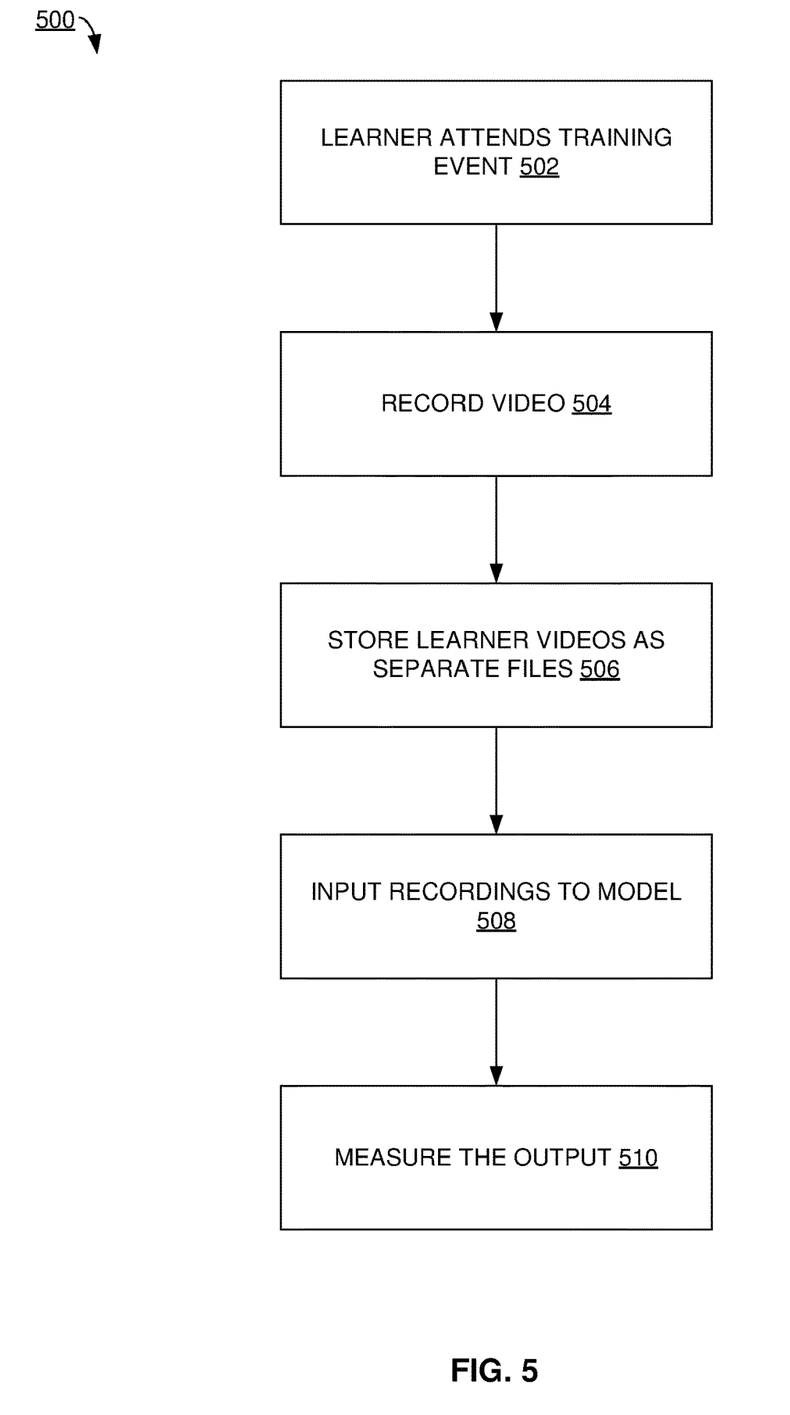
FIG. 5 illustrates another example system architecture that can facilitate information extraction from live online sessions, in accordance with an embodiment of this disclosure.

FIG. 5 illustrates another example system architecture 500 that can facilitate information extraction from live online sessions, in accordance with an embodiment of this disclosure. In some examples, parts of system architecture 400 can be implemented in information extraction from live online sessions component 112 of FIG. 1.

System architecture 500 comprises learner attends training event 502, record video 504, store learner videos as separate files 506, input recordings to model 508, and measure output 510.

Learner attends training event 502 can comprise a user of client computer 104A of FIG. 1 logging into an online session provided by online session component 110. Record video 504 can comprise information extraction from live online sessions component 112 recording a video of the online session. In some examples, a virtual agent can capture and record facial expressions from learners.

Store learner videos as separate files 506 can comprise information extraction from live online sessions component 112 dividing the video from record video 504 into multiple parts, where videos of respective users are in separate parts. In some examples, the videos can be stored as separate files, as a series of frames. Input recordings to model 508 can comprise information extraction from live online sessions component 112 providing these separate videos to information extraction from live online sessions neural network model 114. Where the videos are stored as files comprising frames, this can comprise passing the frames into the model per learner and capturing the outputs.

Measure output 510 can comprise measuring a corresponding output from the model, such as one that identifies a particular learner's engagement over the course of the recording.

Recordings of learners can be stored as separate files per learner, and timestamped along with a recording of a learning event. These files can be fed into a CNN LSTM model, with an output of the model being a classification of engagement level based on the learner's facial expressions. By leveraging a CNN LSTM architecture, feature extraction of recordings of learners can be performed while maintaining a temporal position of frames, and analyzing a series of images, as opposed to a frame-by-frame analysis. These classifications can be reported across multiple learning events being leveraged to identify gaps and high points in learner engagement.

Example Process Flows

FIG. 6 illustrates an example process flow 600 that can facilitate information extraction from live online sessions, in accordance with an embodiment of this disclosure. In some examples, one or more embodiments of process flow 600 can be implemented by information extraction from live online sessions component 112 of FIG. 1, or computing environment 900 of FIG. 9.

It can be appreciated that the operating procedures of process flow 600 are example operating procedures, and that there can be embodiments that implement more or fewer operating procedures than are depicted, or that implement the depicted operating procedures in a different order than as depicted. In some examples, process flow 600 can be implemented in conjunction with one or more embodiments of one or more of process flow 700 of FIG. 7, and/or process flow 800 of FIG. 8.

Process flow 600 begins with 602, and moves to operation 604. Operation 604 depicts identifying time-series bio telemetry data that corresponds to a first user of an online session, wherein the time-series bio telemetry data identifies a first user engagement of the first user. This can comprise capturing a user's bio telemetry data at bio telemetry device 102A of FIG. 1, and passing it through client computer 104A to information extraction from live online sessions component 112.

In some examples, the time-series bio telemetry data comprises time-series electroencephalography data.

After operation 604, process flow 600 moves to operation 606.

Operation 606 depicts identifying a first video recording of the online session, wherein the first video recording is representative of a first video of the first user. This can comprise information extraction from live online sessions component 112 of FIG. 1 storing a recording of an online session that is facilitated by online session component 110.

In some examples, the first video recording is representative of a third video of a third user, and identifying the first video recording of the online session comprises storing a first portion of the first video recording that corresponds to the first user as a first file, and storing a second portion of the first video recording that corresponds to the third user as a second file. That is, a separate video file can be stored for each user in a source video of an online session.

In some examples, the first file comprises a first timestamp. That is, each user video can be timestamped. In some examples, the first video recording is stored as a third file, and wherein the third file is separate from each of the first file and the second file. That is, in addition to storing user-specific video files, the original video can also be stored.

After operation 606, process flow 600 moves to operation 608.

Operation 608 depicts inputting the time-series bio telemetry data and the first video recording as a first input to a neural network model to produce a trained neural network model, wherein the trained neural network model is configured to classify a second user engagement from a second video recording representative of a second video of a second user. This can comprise using the bio telemetry data and the online session recording to train information extraction from live online sessions neural network model 114 of FIG. 1 to identify user engagement based on a video of the user.

In some examples, the neural network model comprises a convolutional neural network long-short term memory model.

In some examples, the first video recording is represented in a first format and is generated by a first online session application, wherein the second video recording is represented in a second format that is generated by a second online session application, and wherein the first format differs from the second format. That is, information extraction from live online sessions neural network model 114 of FIG. 1 can be platform agnostic, and can identify user engagement during online sessions conducted via a variety of online session platforms.

After operation 608, process flow 600 moves to operation 610.

Operation 610 depicts classifying the second user engagement of the second user comprising inputting the second video recording as a second input to the trained neural network model. That is, once information extraction from live online sessions neural network model 114 of FIG. 1 is trained, it can be provided videos of a user's online session as input, and output an identification of the user's engagement during the session.

After operation 610, process flow 600 moves to 612, where process flow 600 ends.

FIG. 7 illustrates an example process flow 700 that can facilitate information extraction from live online sessions, in accordance with an embodiment of this disclosure. In some examples, one or more embodiments of process flow 700 can be implemented by information extraction from live online sessions component 112 of FIG. 1, or computing environment 900 of FIG. 9.

It can be appreciated that the operating procedures of process flow 700 are example operating procedures, and that there can be embodiments that implement more or fewer operating procedures than are depicted, or that implement the depicted operating procedures in a different order than as depicted. In some examples, process flow 700 can be implemented in conjunction with one or more embodiments of one or more of process flow 600 of FIG. 6, and/or process flow 800 of FIG. 8.

Process flow 700 begins with 702, and moves to operation 704. Operation 704 depicts identifying time-series bio telemetry data that corresponds to a first user of an online session. In some examples, operation 704 can be implemented in a similar manner as operation 604 of FIG. 6.

After operation 704, process flow 700 moves to operation 706.

Operation 706 depicts identifying a first video recording of the first user of the online session. In some examples, operation 706 can be implemented in a similar manner as operation 606 of FIG. 6.

After operation 706, process flow 700 moves to operation 708.

Operation 708 depicts providing the time-series bio telemetry data and the first video recording as a first input to a neural network model to produce a trained neural network model, wherein the trained neural network model is configured to classify user engagement from a second video recording of a second user. In some examples, operation 708 can be implemented in a similar manner as operation 608 of FIG. 6.

In some examples, the time-series bio telemetry data comprises brain alpha wave values of the first user and brain beta wave values of the first user. This can be similar to information of system architecture 400 of FIG. 4.

In some examples, operation 708 comprises determining an engagement value for the first user based on the brain alpha wave values and the brain beta wave values. That is, user engagement can be determined based on alpha and beta waves. In some examples, the engagement value is a first engagement value, and operation 708 comprises normalizing a first range over which the first engagement value is able to vary relative to a second range over which a second engagement value for the second user is able to vary. That is, alpha and beta wave vales can be normalized, such as to vary over [0, 1].

After operation 708, process flow 700 moves to operation 710.

Operation 710 depicts classifying the user engagement of the second user based on an output from providing the second video as a second input to the trained neural network model. In some examples, operation 710 can be implemented in a similar manner as operation 610 of FIG. 6.

In some examples, operation 710 comprises generating a transcript of spoken dialogue of the second video recording, and classifying the user engagement of the second user comprises identifying a discussion topic in the transcript that corresponds to the user engagement meeting a threshold criterion. That is, times of particular user engagement can be correlated to a subject being discussed at that time via the transcript.

In some examples, the transcript comprises text that appears in the first video recording. That is, the transcript can capture spoken text in the online session, as well as text that appears on screen in the online session.

In some examples, the first video recording comprises frames of video, and wherein the neural network model is separately trained using each frame of video of the frames of video. That is, data can be pre-stored in a timestamped format so that a temporal position of video frames can remain consistent. Information extraction from live online sessions neural network model 114 of FIG. 1 can analyze patterns across frames of a video. So, frames can be provided to information extraction from live online sessions neural network model 114 in a correct temporal order. A CNN LSTM architecture can learn patterns in frame sequences and use these identified patterns to capture a state of a single frame, as well as its relation to past frames.

After operation 710, process flow 700 moves to 712, where process flow 700 ends.

FIG. 8 illustrates an example process flow 800 that can facilitate information extraction from live online sessions, in accordance with an embodiment of this disclosure. In some examples, one or more embodiments of process flow 800 can be implemented by information extraction from live online sessions component 112 of FIG. 1, or computing environment 900 of FIG. 9.

It can be appreciated that the operating procedures of process flow 800 are example operating procedures, and that there can be embodiments that implement more or fewer operating procedures than are depicted, or that implement the depicted operating procedures in a different order than as depicted. In some examples, process flow 800 can be implemented in conjunction with one or more embodiments of one or more of process flow 600 of FIG. 6, and/or process flow 700 of FIG. 7.

Process flow 800 begins with 802, and moves to operation 804. Operation 804 depicts identifying time-series bio telemetry data associated with a first user of an online session. In some examples, operation 804 can be implemented in a similar manner as operation 604 of FIG. 6.

After operation 804, process flow 800 moves to operation 806.

Operation 806 depicts accessing a first video recording comprising a first video of the online session. In some examples, operation 806 can be implemented in a similar manner as operation 606 of FIG. 6.

In some examples, the first video recording further comprises a third video of a third user and operation 806 comprises storing a first portion of the first video recording that corresponds to the first user as a first file, and storing a second portion of the first video recording that corresponds to the third user as a second file. That is, a separate video file can be stored for each user in an online session.

After operation 806, process flow 800 moves to operation 808.

Operation 808 depicts based on the time-series bio telemetry data and the first video recording, training a neural network model to produce a trained neural network model that is configured to classify user engagement of different users. In some examples, operation 808 can be implemented in a similar manner as operation 608 of FIG. 6.

After operation 808, process flow 800 moves to operation 810.

Operation 810 depicts classifying a user engagement of a second user based on a result of inputting a second video of the second user to the trained neural network model. In some examples, operation 810 can be implemented in a similar manner as operation 610 of FIG. 6.

In some examples, the trained neural network model is configured to classify an engagement level of a second user, who is determined to be depicted in the second video recording based on facial expressions of the second user in the second video recording.

In some examples, the first video recording is in a first format and is generated by a first online session application, wherein the second video recording is in a second format that is generated by a second online session application, and wherein the first format differs from the second format. That is, the present techniques for analyzing user engagement can be platform agnostic regarding an online session program used.

In some examples, the first file comprises a first timestamp. In some examples, the first video recording is stored as a third file, and wherein the third file is separate from each of the first file and the second file. That is, an original video can be stored along with user-specific videos.

After operation 810, process flow 800 moves to 812, where process flow 800 ends.

Example Operating Environment

In order to provide additional context for various embodiments described herein, FIG. 9 and the following discussion are intended to provide a brief, general description of a suitable computing environment 900 in which the various embodiments of the embodiment described herein can be implemented.

For example, parts of computing environment 900 can be used to implement one or more embodiments of bio telemetry device 102A, bio telemetry device 102B, client computer 104A, client computer 104B, and/or server 108 of FIG. 1.

In some examples, computing environment 900 can implement one or more embodiments of the process flows of FIGS. 6-8 to facilitate information extraction from live online sessions.

While the embodiments have been described above in the general context of computer-executable instructions that can run on one or more computers, those skilled in the art will recognize that the embodiments can be also implemented in combination with other program modules and/or as a combination of hardware and software.

Generally, program modules include routines, programs, components, data structures, etc., that perform particular tasks or implement particular abstract data types. Moreover, those skilled in the art will appreciate that the various methods can be practiced with other computer system configurations, including single-processor or multiprocessor computer systems, minicomputers, mainframe computers, Internet of Things (IoT) devices, distributed computing systems, as well as personal computers, hand-held computing devices, microprocessor-based or programmable consumer electronics, and the like, each of which can be operatively coupled to one or more associated devices.

The illustrated embodiments of the embodiments herein can be also practiced in distributed computing environments where certain tasks are performed by remote processing devices that are linked through a communications network. In a distributed computing environment, program modules can be located in both local and remote memory storage devices.

Computing devices typically include a variety of media, which can include computer-readable storage media, machine-readable storage media, and/or communications media, which two terms are used herein differently from one another as follows. Computer-readable storage media or machine-readable storage media can be any available storage media that can be accessed by the computer and includes both volatile and nonvolatile media, removable and non-removable media. By way of example, and not limitation, computer-readable storage media or machine-readable storage media can be implemented in connection with any method or technology for storage of information such as computer-readable or machine-readable instructions, program modules, structured data or unstructured data.

Computer-readable storage media can include, but are not limited to, random access memory (RAM), read only memory (ROM), electrically erasable programmable read only memory (EEPROM), flash memory or other memory technology, compact disk read only memory (CD-ROM), digital versatile disk (DVD), Blu-ray disc (BD) or other optical disk storage, magnetic cassettes, magnetic tape, magnetic disk storage or other magnetic storage devices, solid state drives or other solid state storage devices, or other tangible and/or non-transitory media which can be used to store desired information. In this regard, the terms "tangible" or "non-transitory" herein as applied to storage, memory or computer-readable media, are to be understood to exclude only propagating transitory signals per se as modifiers and do not relinquish rights to all standard storage, memory or computer-readable media that are not only propagating transitory signals per se.

Computer-readable storage media can be accessed by one or more local or remote computing devices, e.g., via access requests, queries or other data retrieval protocols, for a variety of operations with respect to the information stored by the medium.

Communications media typically embody computer-readable instructions, data structures, program modules or other structured or unstructured data in a data signal such as a modulated data signal, e.g., a carrier wave or other transport mechanism, and includes any information delivery or transport media. The term "modulated data signal" or signals refers to a signal that has one or more of its characteristics set or changed in such a manner as to encode information in one or more signals. By way of example, and not limitation, communication media include wired media, such as a wired network or direct-wired connection, and wireless media such as acoustic, RF, infrared and other wireless media.

With reference again to FIG. 9, the example environment 900 for implementing various embodiments described herein includes a computer 902, the computer 902 including a processing unit 904, a system memory 906 and a system bus 908. The system bus 908 couples system components including, but not limited to, the system memory 906 to the processing unit 904. The processing unit 904 can be any of various commercially available processors. Dual microprocessors and other multi-processor architectures can also be employed as the processing unit 904.

The system bus 908 can be any of several types of bus structure that can further interconnect to a memory bus (with or without a memory controller), a peripheral bus, and a local bus using any of a variety of commercially available bus architectures. The system memory 906 includes ROM 910 and RAM 912. A basic input/output system (BIOS) can be stored in a nonvolatile storage such as ROM, erasable programmable read only memory (EPROM), EEPROM, which BIOS contains the basic routines that help to transfer information between elements within the computer 902, such as during startup. The RAM 912 can also include a high-speed RAM such as static RAM for caching data.

The computer 902 further includes an internal hard disk drive (HDD) 914 (e.g., EIDE, SATA), one or more external storage devices 916 (e.g., a magnetic floppy disk drive (FDD) 916, a memory stick or flash drive reader, a memory card reader, etc.) and an optical disk drive 920 (e.g., which can read or write from a CD-ROM disc, a DVD, a BD, etc.). While the internal HDD 914 is illustrated as located within the computer 902, the internal HDD 914 can also be configured for external use in a suitable chassis (not shown). Additionally, while not shown in environment 900, a solid state drive (SSD) could be used in addition to, or in place of, an HDD 914. The HDD 914, external storage device(s) 916 and optical disk drive 920 can be connected to the system bus 908 by an HDD interface 924, an external storage interface 926 and an optical drive interface 928, respectively. The interface 924 for external drive implementations can include at least one or both of Universal Serial Bus (USB) and Institute of Electrical and Electronics Engineers (IEEE) 1394 interface technologies. Other external drive connection technologies are within contemplation of the embodiments described herein.

The drives and their associated computer-readable storage media provide nonvolatile storage of data, data structures, computer-executable instructions, and so forth. For the computer 902, the drives and storage media accommodate the storage of any data in a suitable digital format. Although the description of computer-readable storage media above refers to respective types of storage devices, it should be appreciated by those skilled in the art that other types of storage media which are readable by a computer, whether presently existing or developed in the future, could also be used in the example operating environment, and further, that any such storage media can contain computer-executable instructions for performing the methods described herein.

A number of program modules can be stored in the drives and RAM 912, including an operating system 930, one or more application programs 932, other program modules 934 and program data 936. All or portions of the operating system, applications, modules, and/or data can also be cached in the RAM 912. The systems and methods described herein can be implemented utilizing various commercially available operating systems or combinations of operating systems.

Computer 902 can optionally comprise emulation technologies. For example, a hypervisor (not shown) or other intermediary can emulate a hardware environment for operating system 930, and the emulated hardware can optionally be different from the hardware illustrated in FIG. 9. In such an embodiment, operating system 930 can comprise one virtual machine (VM) of multiple VMs hosted at computer 902. Furthermore, operating system 930 can provide runtime environments, such as the Java runtime environment or the .NET framework, for applications 932. Runtime environments are consistent execution environments that allow applications 932 to run on any operating system that includes the runtime environment. Similarly, operating system 930 can support containers, and applications 932 can be in the form of containers, which are lightweight, standalone, executable packages of software that include, e.g., code, runtime, system tools, system libraries and settings for an application.

Further, computer 902 can be enable with a security module, such as a trusted processing module (TPM). For instance, with a TPM, boot components hash next in time boot components, and wait for a match of results to secured values, before loading a next boot component. This process can take place at any layer in the code execution stack of computer 902, e.g., applied at the application execution level or at the operating system (OS) kernel level, thereby enabling security at any level of code execution.

A user can enter commands and information into the computer 902 through one or more wired/wireless input devices, e.g., a keyboard 938, a touch screen 940, and a pointing device, such as a mouse 942. Other input devices (not shown) can include a microphone, an infrared (IR) remote control, a radio frequency (RF) remote control, or other remote control, a joystick, a virtual reality controller and/or virtual reality headset, a game pad, a stylus pen, an image input device, e.g., camera(s), a gesture sensor input device, a vision movement sensor input device, an emotion or facial detection device, a biometric input device, e.g., fingerprint or iris scanner, or the like. These and other input devices are often connected to the processing unit 904 through an input device interface 944 that can be coupled to the system bus 908, but can be connected by other interfaces, such as a parallel port, an IEEE 1394 serial port, a game port, a USB port, an IR interface, a BLUETOOTH® interface, etc.

A monitor 946 or other type of display device can be also connected to the system bus 908 via an interface, such as a video adapter 948. In addition to the monitor 946, a computer typically includes other peripheral output devices (not shown), such as speakers, printers, etc.

The computer 902 can operate in a networked environment using logical connections via wired and/or wireless communications to one or more remote computers, such as a remote computer(s) 950. The remote computer(s) 950 can be a workstation, a server computer, a router, a personal computer, portable computer, microprocessor-based entertainment appliance, a peer device or other common network node, and typically includes many or all of the elements described relative to the computer 902, although, for purposes of brevity, only a memory/storage device 952 is illustrated. The logical connections depicted include wired/wireless connectivity to a local area network (LAN) 954 and/or larger networks, e.g., a wide area network (WAN) 956. Such LAN and WAN networking environments are commonplace in offices and companies, and facilitate enterprise-wide computer networks, such as intranets, all of which can connect to a global communications network, e.g., the Internet.

When used in a LAN networking environment, the computer 902 can be connected to the local network 954 through a wired and/or wireless communication network interface or adapter 958. The adapter 958 can facilitate wired or wireless communication to the LAN 954, which can also include a wireless access point (AP) disposed thereon for communicating with the adapter 958 in a wireless mode.

When used in a WAN networking environment, the computer 902 can include a modem 960 or can be connected to a communications server on the WAN 956 via other means for establishing communications over the WAN 956, such as by way of the Internet. The modem 960, which can be internal or external and a wired or wireless device, can be connected to the system bus 908 via the input device interface 944. In a networked environment, program modules depicted relative to the computer 902 or portions thereof, can be stored in the remote memory/storage device 952. It will be appreciated that the network connections shown are example and other means of establishing a communications link between the computers can be used.

When used in either a LAN or WAN networking environment, the computer 902 can access cloud storage systems or other network-based storage systems in addition to, or in place of, external storage devices 916 as described above. Generally, a connection between the computer 902 and a cloud storage system can be established over a LAN 954 or WAN 956 e.g., by the adapter 958 or modem 960, respectively. Upon connecting the computer 902 to an associated cloud storage system, the external storage interface 926 can, with the aid of the adapter 958 and/or modem 960, manage storage provided by the cloud storage system as it would other types of external storage. For instance, the external storage interface 926 can be configured to provide access to cloud storage sources as if those sources were physically connected to the computer 902.

The computer 902 can be operable to communicate with any wireless devices or entities operatively disposed in wireless communication, e.g., a printer, scanner, desktop and/or portable computer, portable data assistant, communications satellite, any piece of equipment or location associated with a wirelessly detectable tag (e.g., a kiosk, news stand, store shelf, etc.), and telephone. This can include Wireless Fidelity (Wi-Fi) and BLUETOOTH® wireless technologies. Thus, the communication can be a predefined structure as with a conventional network or simply an ad hoc communication between at least two devices.

CONCLUSION

As it employed in the subject specification, the term "processor" can refer to substantially any computing processing unit or device comprising, but not limited to comprising, single-core processors; single-processors with software multithread execution capability; multi-core processors; multi-core processors with software multithread execution capability; multi-core processors with hardware multithread technology; parallel platforms; and parallel platforms with distributed shared memory in a single machine or multiple machines. Additionally, a processor can refer to an integrated circuit, a state machine, an application specific integrated circuit (ASIC), a digital signal processor (DSP), a programmable gate array (PGA) including a field programmable gate array (FPGA), a programmable logic controller (PLC), a complex programmable logic device (CPLD), a discrete gate or transistor logic, discrete hardware components, or any combination thereof designed to perform the functions described herein. Processors can exploit nano-scale architectures such as, but not limited to, molecular and quantum-dot based transistors, switches and gates, in order to optimize space usage or enhance performance of user equipment. A processor may also be implemented as a combination of computing processing units. One or more processors can be utilized in supporting a virtualized computing environment. The virtualized computing environment may support one or more virtual machines representing computers, servers, or other computing devices. In such virtualized virtual machines, components such as processors and storage devices may be virtualized or logically represented. For instance, when a processor executes instructions to perform "operations", this could include the processor performing the operations directly and/or facilitating, directing, or cooperating with another device or component to perform the operations.

In the subject specification, terms such as "datastore," "data storage," "database," "cache," and substantially any other information storage component relevant to operation and functionality of a component, refer to "memory components," or entities embodied in a "memory" or components comprising the memory. It will be appreciated that the memory components, or computer-readable storage media, described herein can be either volatile memory or nonvolatile storage, or can include both volatile and nonvolatile storage. By way of illustration, and not limitation, nonvolatile storage can include ROM, programmable ROM (PROM), EPROM, EEPROM, or flash memory. Volatile memory can include RAM, which acts as external cache memory. By way of illustration and not limitation, RAM can be available in many forms such as synchronous RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), and direct Rambus RAM (DRRAM). Additionally, the disclosed memory components of systems or methods herein are intended to comprise, without being limited to comprising, these and any other suitable types of memory.

The illustrated embodiments of the disclosure can be practiced in distributed computing environments where certain tasks are performed by remote processing devices that are linked through a communications network. In a distributed computing environment, program modules can be located in both local and remote memory storage devices.

The systems and processes described above can be embodied within hardware, such as a single integrated circuit (IC) chip, multiple ICs, an ASIC, or the like. Further, the order in which some or all of the process blocks appear in each process should not be deemed limiting. Rather, it should be understood that some of the process blocks can be executed in a variety of orders that are not all of which may be explicitly illustrated herein.

As used in this application, the terms "component," "module," "system," "interface," "cluster," "server," "node," or the like are generally intended to refer to a computer-related entity, either hardware, a combination of hardware and software, software, or software in execution or an entity related to an operational machine with one or more specific functionalities. For example, a component can be, but is not limited to being, a process running on a processor, a processor, an object, an executable, a thread of execution, computer-executable instruction(s), a program, and/or a computer. By way of illustration, both an application running on a controller and the controller can be a component. One or more components may reside within a process and/or thread of execution and a component may be localized on one computer and/or distributed between two or more computers. As another example, an interface can include input/output (I/O) components as well as associated processor, application, and/or application programming interface (API) components.

Further, the various embodiments can be implemented as a method, apparatus, or article of manufacture using standard programming and/or engineering techniques to produce software, firmware, hardware, or any combination thereof to control a computer to implement one or more embodiments of the disclosed subject matter. An article of manufacture can encompass a computer program accessible from any computer-readable device or computer-readable storage/communications media. For example, computer readable storage media can include but are not limited to magnetic storage devices (e.g., hard disk, floppy disk, magnetic strips . . . ), optical discs (e.g., CD, DVD . . . ), smart cards, and flash memory devices (e.g., card, stick, key drive . . . ). Of course, those skilled in the art will recognize many modifications can be made to this configuration without departing from the scope or spirit of the various embodiments.

In addition, the word "example" or "exemplary" is used herein to mean serving as an example, instance, or illustration. Any embodiment or design described herein as "exemplary" is not necessarily to be construed as preferred or advantageous over other embodiments or designs. Rather, use of the word exemplary is intended to present concepts in a concrete fashion. As used in this application, the term "or" is intended to mean an inclusive "or" rather than an exclusive "or." That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims should generally be construed to mean "one or more" unless specified otherwise or clear from context to be directed to a singular form.

What has been described above includes examples of the present specification. It is, of course, not possible to describe every conceivable combination of components or methods for purposes of describing the present specification, but one of ordinary skill in the art may recognize that many further combinations and permutations of the present specification are possible. Accordingly, the present specification is intended to embrace all such alterations, modifications and variations that fall within the spirit and scope of the appended claims. Furthermore, to the extent that the term "includes" is used in either the detailed description or the claims, such term is intended to be inclusive in a manner similar to the term "comprising" as "comprising" is interpreted when employed as a transitional word in a claim.

What is claimed is:

1. A system, comprising:
   a processor; and
   a memory that stores executable instructions that, when executed by the processor, facilitate performance of operations, comprising:
      identifying time-series bio telemetry data that corresponds to a first user of an online session, wherein the time-series bio telemetry data identifies a first user engagement of the first user;
      identifying a first video recording of the online session, wherein the first video recording is representative of a first video of the first user;
      inputting the time-series bio telemetry data and the first video recording as a first input to a neural network model to produce a trained neural network model, wherein the trained neural network model is configured to classify a second user engagement from a second video recording representative of a second video of a second user; and
      classifying the second user engagement of the second user comprising inputting the second video recording as a second input to the trained neural network model.

2. The system of claim 1, wherein the time-series bio telemetry data comprises time-series electroencephalography data.

3. The system of claim 1, wherein the neural network model comprises a convolutional neural network long-short term memory model.

4. The system of claim 1, wherein the first video recording is represented in a first format and is generated by a first online session application, wherein the second video recording is represented in a second format that is generated by a second online session application, and wherein the first format differs from the second format.

5. The system of claim 1, wherein the first video recording is representative of a third video of a third user, and wherein identifying the first video recording of the online session comprises:
   storing a first portion of the first video recording that corresponds to the first user as a first file; and
   storing a second portion of the first video recording that corresponds to the third user as a second file.

6. The system of claim 5, wherein the first file comprises a first timestamp.

7. The system of claim 5, wherein the first video recording is stored as a third file, and wherein the third file is separate from each of the first file and the second file.

8. A method, comprising:
- identifying, by a system comprising a processor, time-series bio telemetry data that corresponds to a first user of an online session;
- identifying, by the system, a first video recording of the first user of the online session;
- providing, by the system, the time-series bio telemetry data and the first video recording as a first input to a neural network model to produce a trained neural network model, wherein the trained neural network model is configured to classify user engagement from a second video recording of a second user; and
- classifying, by the system, the user engagement of the second user based on an output from providing the second video as a second input to the trained neural network model.

9. The method of claim 8, wherein the time-series bio telemetry data comprises brain alpha wave values of the first user and brain beta wave values of the first user.

10. The method of claim 9, further comprising:
- determining, by the system, an engagement value for the first user based on the brain alpha wave values and the brain beta wave values.

11. The method of claim 10, wherein the engagement value is a first engagement value, and further comprising:
- normalizing, by the system, a first range over which the first engagement value is able to vary relative to a second range over which a second engagement value for the second user is able to vary.

12. The method of claim 8, further comprising:
- generating, by the system, a transcript of spoken dialogue of the second video recording; and
- wherein classifying the user engagement of the second user comprises identifying a discussion topic in the transcript that corresponds to the user engagement meeting a threshold criterion.

13. The method of claim 12, wherein the transcript comprises text that appears in the first video recording.

14. The method of claim 8, wherein the first video recording comprises frames of video, and wherein the neural network model is separately trained using each frame of video of the frames of video.

15. A non-transitory computer-readable medium comprising instructions that, in response to execution, cause a system comprising a processor to perform operations, comprising:
- identifying time-series bio telemetry data associated with a first user of an online session;
- accessing a first video recording comprising a first video of the online session;
- based on the time-series bio telemetry data and the first video recording, training a neural network model to produce a trained neural network model that is configured to classify user engagement of different users; and
- classifying a user engagement of a second user based on a result of inputting a second video of the second user to the trained neural network model.

16. The non-transitory computer-readable medium of claim 15, wherein the trained neural network model is configured to classify an engagement level of a second user, who is determined to be depicted in the second video recording based on facial expressions of the second user in the second video recording.

17. The non-transitory computer-readable medium of claim 15, wherein the first video recording is in a first format and is generated by a first online session application, wherein the second video recording is in a second format that is generated by a second online session application, and wherein the first format differs from the second format.

18. The non-transitory computer-readable medium of claim 15, wherein the first video recording further comprises a third video of a third user and wherein accessing the first video recording of the online session comprises:
- storing a first portion of the first video recording that corresponds to the first user as a first file; and
- storing a second portion of the first video recording that corresponds to the third user as a second file.

19. The non-transitory computer-readable medium of claim 18, wherein the first file comprises a first timestamp.

20. The non-transitory computer-readable medium of claim 18, wherein the first video recording is stored as a third file, and wherein the third file is separate from each of the first file and the second file.

* * * * *